US012618168B2

(12) United States Patent  
Gassner et al.

(10) Patent No.: US 12,618,168 B2  
(45) Date of Patent: *May 5, 2026

(54) METHOD FOR SURFACE TREATMENT AND/OR PRODUCTION OF A MEDICAL PRODUCT, AND A MEDICAL PRODUCT

(71) Applicant: Aesculap AG, Tuttlingen (DE)

(72) Inventors: Andreas Gassner, Tuttlingen (DE); Lukas Waidelich, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 463 days.

This patent is subject to a terminal disclaimer.

(21) Appl. No.: 17/917,157

(22) PCT Filed: Apr. 1, 2021

(86) PCT No.: PCT/EP2021/058723  
§ 371 (c)(1),  
(2) Date: Oct. 5, 2022

(87) PCT Pub. No.: WO2021/204702  
PCT Pub. Date: Oct. 14, 2021

(65) Prior Publication Data  
US 2023/0160090 A1 May 25, 2023

(30) Foreign Application Priority Data  
Apr. 6, 2020 (DE) .................... 10 2020 204 431.7

(51) Int. Cl.  
*C25F 3/06* (2006.01)  
*A61B 17/00* (2006.01)

(52) U.S. Cl.  
CPC .............. *C25F 3/06* (2013.01); *A61B 17/00* (2013.01); *A61B 2017/00526* (2013.01)

(58) Field of Classification Search  
CPC ...... A61B 17/00; A61B 17/00526; C25F 3/06  
See application file for complete search history.

(56) References Cited

U.S. PATENT DOCUMENTS

| | | | | |
|---|---|---|---|---|
| 2,461,035 A | * | 2/1949 | Clingan .................... | C25F 3/24 |
| | | | | 205/677 |
| 5,057,108 A | | 10/1991 | Shetty et al. | |
| 8,518,234 B2 | | 8/2013 | Rakowski | |
| 9,504,554 B2 | | 11/2016 | Bayer et al. | |
| 2005/0057004 A1 | * | 3/2005 | Yamazaki ................. | C25F 3/06 |
| | | | | 277/592 |
| 2007/0193326 A1 | | 8/2007 | Bogart et al. | |
| 2009/0217626 A1 | * | 9/2009 | Kemp ...................... | A61L 2/24 |
| | | | | 53/97 |
| 2017/0114472 A1 | * | 4/2017 | Choi ......................... | C25F 3/06 |
| 2018/0375116 A1 | | 12/2018 | Yano et al. | |
| 2022/0002896 A1 | | 1/2022 | Bayer et al. | |
| 2022/0008622 A1 | | 1/2022 | Turner et al. | |

FOREIGN PATENT DOCUMENTS

| | | | |
|---|---|---|---|
| CN | 1846016 | A | 10/2006 |
| CN | 103014814 | A | 4/2013 |
| CN | 107921174 | A | 4/2018 |
| DE | 102004044738 | A1 | 3/2006 |
| DE | 102018218393 | A1 | 4/2020 |
| FR | 2149542 | A1 | 3/1973 |
| JP | 2002509755 | A | 4/2002 |
| JP | 2012177157 | A | 9/2012 |
| JP | 2017503921 | A | 2/2017 |
| JP | WO2017110656 | A1 | 12/2017 |
| KR | 20180107422 | A | 10/2018 |
| RU | 2046158 | C1 | 10/1995 |
| SE | 143429 | C1 | 11/1953 |
| WO | 9949795 | A1 | 10/1999 |
| WO | 2015092133 | A1 | 6/2015 |

OTHER PUBLICATIONS

Stöver, M., Renke-Gluszko, M., Schratzenstaller, T. et al. Microstructuring of stainless steel implants by electrochemical etching. J Mater Sci 41, 5569-5575 (Year: 2006).*

Kikrup J. "From flint to stainless steel: observations on surgical instrument composition." Ann R Coll Surg Engl. 1993, 75, 5, 365-374. (Year: 2025).*

Han, Wei; Fang, Fengzhou. "Two-step electropolishing of 316L stainless steel in a sulfuric acid-free electrolyte." Journal of Materials Processing Technology, 2020, 279, 116558 (Year: 2025).*

Han, Wei; Fang, Fengzhou. "Two-step electropolishing of 316L stainless steel in a sulfuric acid-free electrolyte." Journal of Materials Processing Technology, 2020, 279, 116558 (Year: 2020).*

Search Report received in International Application No. PCT/EP2021/058723 dated Jun. 29, 2021, with translation, 8 pages.

Stoever et al., "Microstructuring of stainless steel implants by electrochemical etching," J. Mater Sci (2006), Jun. 20, 2006, 8 pages.

GS1 UK, Healthcare User Group, "Technologies for Marking Surgical Instruments", 2017, 8 pages.

Office Action received in Chinese Application No. 202180040820.1 dated May 27, 2025, with translation, 17 pages.

Shiying, "Household Appliance Technology," China Machine Press, Jul. 31, 1994, with translation, 7 pages.

* cited by examiner

*Primary Examiner* — Brian W Cohen  
*Assistant Examiner* — Nathanael Jason Downes  
(74) *Attorney, Agent, or Firm* — CM Law; Christopher A. Rothe

(57) ABSTRACT

A medical product and a method of surface treatment and/or manufacture of the medical product. The method includes the step of electrochemically etching the medical product. The medical product can include a metal or alloy and have one or more of the following features:

a pitting corrosion potential of 100 mV to 1200 mV, a contact angle of 90° to 140°, and a passive layer having a thickness of 1 nm to 10 nm that coats at least sections of the surface of the medical product.

23 Claims, No Drawings

METHOD FOR SURFACE TREATMENT AND/OR PRODUCTION OF A MEDICAL PRODUCT, AND A MEDICAL PRODUCT

CROSS-REFERENCE TO RELATED APPLICATIONS

This application is the United States national stage entry of International Application No. PCT/EP2021/058723, filed Apr. 1, 2021, and claims priority to German Application No. 10 2020 204 431.7, filed Apr. 6, 2020. The contents of International Application No. PCT/EP2021/058723 and German Application No. 10 2020 204 431.7 are incorporated by reference herein in their entireties.

FIELD

The invention relates to a method of surface treatment or processing and/or manufacture of a medical product and to a medical product.

BACKGROUND

Medical products, such as surgical instruments in particular, are generally subjected to a surface treatment before they are complete. For this purpose, the surfaces of the products can be processed, for example, by means of slide finishing and/or belt finishing. This can eliminate defects in the parent material and/or forging-related defects, for example decarburized regions, or surface defects, for example pores, scars or cracks, which would otherwise have an adverse effect on the corrosion resistance of the products.

However, belt finishing can give rise to fine notches or elevations on the product surface. These can be turned over or flattened in a subsequent treatment step. This can give rise to doubled-over material. Moreover, there can be isolated instances of material transfer, for example of silicon oxide particles, from an abrasive belt to the product surface. Such material transfer and the stress on the medical product associated with the mechanical processing can in turn generate or increase intrinsic stresses in the product. An additional problem is that surface defects in the product that have not been eliminated or generated in the grinding operation can be eliminated only to a limited degree in a downstream treatment step.

Dulling of a medical product can be accomplished using spherical blasting agents, for example glass beads. This results in plastic deformation of the product surface, by means of which it is increased in size and roughened. Since glass beads are generally very hard (Mohs hardness of 6) and are brittle as well, some degree of breakage of the blasting agent will occur over time. As a result, both spherical glass beads and broken glass beads will hit the surface of the product during the dulling step. While broken glass beads will create sharp notches on the product surface, unbroken glass beads will leave spherical indentations on the surface of the product. As a result of the impact of broken and unbroken glass beads, there is an interaction between the product surface notched by the broken glass beads and the product surface smoothed by the unbroken glass beads. This can likewise result in doubled-over material. In addition to the plastic deformation and the associated generation of intrinsic stresses, material transfer of the blasting agent to the product surface can take place. This material transfer is particularly significant in the region of notches, in which accumulated glass bead material can remain.

As an alternative to the blasting agent treatment described above using the example of glass beads, it is possible to brush the surfaces of medical products. For this purpose, the product surfaces may be processed with brushing disks, for example with the aid of a disk-shaped abrasive pad or of nylon fibers in a disk arrangement with abrasive particles. Aluminum oxide and/or silicon oxide particles have typically been applied to the brushing disks. A brushing step increases the corrosion resistance of the product surface by comparison with a dulled product surface, but a disadvantage is that brushed product surfaces have greater reflection characteristics than dulled product surfaces.

It is also known that microstructures or notches formed by doubled-over material on a product surface and any associated generation or increase of intrinsic stresses in the product have an adverse effect on the corrosion resistance thereof. In the case of material transfer, for example during belt finishing and/or dulling, an additional factor is that the material transferred generates additional microstructures and can cause the weakening of a passivation layer.

SUMMARY

It is an object of the invention to provide a method of surface treatment or processing and/or manufacture of a medical product, which at least partly avoids disadvantages that occur in methods of the generic type and especially leads to a medical product having elevated corrosion resistance and reduced reflection characteristics.

It is a further object of the invention to provide a corresponding medical product.

In a first aspect, the invention relates to a method of surface treatment or processing and/or manufacture of a medical product, wherein the medical product comprises a metal or an alloy or consists of a metal or an alloy. The method comprises the following step:

electrochemically etching the medical product or the surface of the medical product.

The expression "medical product" in the context of the present invention may mean a medical end product, preferably a surgical instrument, or a precursor, especially a semifinished product, a blank or a semifabricated product, a medical end product, preferably a surgical instrument, or a component of a medical end product, preferably of a surgical instrument.

The expression "alloy" in the context of the present invention shall be understood to mean a macroscopically homogeneous metallic material composed of at least two elements (components), of which at least one element is a metal. Accordingly, the expression "alloy" in the context of the present invention may mean a macroscopically homogeneous metallic material consisting of at least two different metals. Alternatively, the expression "alloy" in the context of the present invention may mean a macroscopically homogeneous metallic material consisting of at least one metal and at least one nonmetal, for example carbon.

It has been found that, surprisingly, the disadvantages that occur at the outset in the context of conventional surface treatments of medical products can be partly or even entirely avoided by electrochemical etching of medical products. For instance, using the example of surgical instruments, it has been shown that electrochemical etching brings about a reduction in the reflection of light at the product surface and also an increase in corrosion resistance. In the case of a medical product made from a chromium-containing or chromium-alloyed stainless steel, the basis of the increase in corrosion resistance is more particularly that hexavalent chromium ions go into solution as a result of the electro-chemical etching operation. As a result, chromium-rich oxide layers at the surface of the medical product are removed, which enables direct attack by an acid used for the electrochemical etching operation on chemical and physical inhomogeneities, such as chromium carbide-containing regions around chromium carbides, in the surface of the medical product. This gives rise, especially at sites of former chromium carbide regions, to a microstructure, especially with or in the form of preferably open etching pits, on the surface of the medical product. In addition, it is advantageously possible to break up interfacial regions, especially lath and subblock boundaries, which can especially have the result that individual martensite laths stick out. The result is a roughened product surface at which incident light can be scattered. As a result, the surface of the medical product looks dull, which particularly advantageously simplifies the user-friendliness of the medical product. For example, this can avoid dazzling of a surgeon in an operating theater. The degradation of chromium-depleted regions at the surface of the medical product advantageously also lowers the risk of formation of nucleation sites for pitting corrosion.

A further advantage is that the electrochemical etching operation can promote the formation of a passive layer, especially a thicker passive layer compared to the prior art. As a result, it is additionally possible to increase the corrosion resistance of the medical product.

A further advantage of the electrochemical etching is especially that compressive stresses and tensile stresses and/or doubled-over material and/or overlapping material on the surface of the medical product can be largely or entirely avoided. This can additionally reduce the risk of corrosion.

Moreover, the electrochemical etching can advantageously degrade any corrosion-triggering material defects on the surface of the medical product.

Moreover, the method of the invention, compared to methods of the generic type, advantageously leads to surfaces of the medical product that are of comparable or better cleanability and/or to comparable or better scratch resistance of the medical product and/or to comparable or better mechanical stability of the medical product and/or to comparable or better tactile properties, especially smoothness, of the medical product.

In one embodiment of the invention, the performance of step a) is preceded by a grinding operation, preferably a slide finishing and/or belt finishing operation, on the surface of the medical product.

For slide finishing, the medical product is preferably introduced into a vessel together with slide finishing bodies, preferably in the form of bulk material, or together with an aqueous solution containing slide finishing bodies and optionally additives. The additives optionally provided may be selected from the group consisting of anticorrosives, degreasing agents, pickling agents, separating agents (for example polymer beads having a diameter<1 mm) and mixtures thereof. Such a solution can advantageously take up and transport away abraded material formed by the slide finishing bodies and abraded product. Depending on the additives used in each case, it is additionally possible to achieve further effects, for example protection from corrosion, degreasing and adhesion prophylaxis.

An oscillating or rotating movement of the vessel gives rise to a relative movement between the medical product and the slide finishing bodies. This causes abrasion of material in the medical product, especially at the edges thereof. The surface image of the medical product, roughness, abrasion of material and deburring performance can advantageously be influenced in a controlled manner by machines used for slide finishing, grinding bodies and optional additives.

The slide finishing bodies may comprise a material or consist of a material selected from the group consisting of ceramic, plastic, natural products such as walnut shells, steel and combinations thereof.

In principle, the slide finishing bodies may be of regular and/or irregular shape.

The slide finishing bodies may especially be free of corners and/or edges, for example in ellipsoidal, toroidal or spherical form.

Alternatively or in combination, the slide finishing bodies may have corners and/or edges. In particular, the slide finishing bodies may be polyhedral, for example cubic, cuboidal, prism-shaped, pyramidal or parallelepiped-shaped. In addition, the slide finishing bodies may especially be configured as straight prisms and/or oblique prisms.

Alternatively or in combination, the slide finishing bodies may be conical and/or frustoconical.

In addition, it is possible to use a mixture of different slide finishing bodies for slide finishing of the medical product. For example, it is possible to use corner- and/or edge-free slide finishing bodies and polyhedral slide finishing bodies. Alternatively or in combination, it is possible to use different corner- and/or edge-free slide finishing bodies and/or different polyhedral slide finishing bodies. With regard to possible configurations and shapes, reference is made completely to the configurations and shapes described in the preceding paragraphs for the slide finishing bodies.

The slide finishing bodies may also have at least one dimension, especially at least one average dimension, for example a diameter, especially average diameter, and/or a height, especially average height, and/or a length, especially average length, in the range from 1 mm to 80 mm. The diameter of spherical slide finishing bodies in the context of the present invention shall be understood here to mean twice the radius of a single spherical slide finishing body. By contrast, the diameter of a nonspherical slide finishing body in the context of the present invention shall be understood to mean the greatest possible distance between two points that these can adopt relative to one another along a circumference line of a single nonspherical slide finishing body. The average dimensions mentioned in this paragraph can be determined, for example, by means of bulk density and/or optical measurement. The slide finishing can also be conducted in the form of barrel finishing, vibratory finishing, plunge finishing, drag finishing, centrifugal finishing or pressure flow lapping.

Belt finishing of the medical product is preferably accomplished using abrasive belts. For this purpose, it is especially possible to use abrasive belts that run over at least two rolls. The abrasive belts preferably have a grain size of 150 to 1200. The number of grains is guided here by the measurement unit mesh, i.e. the number of meshes in a grid per inch (25.4 mm). Accordingly, for example, an abrasive with grain size 150 will just pass through a sieve having 150 meshes per inch.

According to the invention, the performance of step a) may be preceded, for example, first by slide finishing and then by belt finishing. Belt finishing may be advantageous in particular with regard to the treatment of what is called a shadow region of the medical product, but also outside such a region. The shadow region defines the region of a medical product in which slide finishing bodies, especially on account of the geometric shape and/or configuration of the medical product, are ineffective or only of limited effectiveness on the surface.

Alternatively, the surface of the medical product may merely be finished by slide finishing prior to the performance of step a). This can avoid the formation of notches and/or elevations on the product surface that originate from belt finishing and, therefore, the corrosion resistance of the medical product can additionally be improved.

Alternatively, the surface of the medical product may merely be finished by belt finishing prior to the performance of step a).

In a further embodiment of the invention, the surface of the medical product is not treated with a blasting agent. As already mentioned, the etching step envisaged in accordance with the invention already advantageously brings about dulling of the surface of the medical product, and therefore any dulling by treatment with a blasting agent is unnecessary. In this way, it is particularly advantageously possible to significantly reduce processing/production times and/or costs for the medical product. Moreover, it is possible in this way to avoid the risk of material transfer from a blasting agent to the medical product, which can additionally improve its corrosion resistance.

Alternatively, the surface of the medical product can be treated with a blasting agent, preferably prior to the performance of step a), especially between grinding, especially slide finishing and/or belt finishing, of the surface of the medical product and the performance of step a). The blasting agent used may especially be a ductile, i.e. non-brittle, blasting agent. The use of such a blasting agent particularly advantageously makes it possible to prevent or at least reduce the creation of notches and/or of microstructures, especially in the form of microscale gaps, on the surface of the medical product. This can avoid or at least reduce the occurrence of local stress peaks in the medical product and in particular can additionally improve the corrosion resistance of the medical product. On top of that, the use of such a blasting agent can advantageously improve the scratch resistance of the medical product. With regard to the grinding mentioned in this paragraph, especially slide finishing and/or belt finishing, of the surface of the medical product, reference is made completely to the corresponding details given in the description so far.

In principle, the blasting agent may comprise a material or consist of a material selected from the group consisting of metal, metal oxide, alloy, ceramic, plastic, plant material, sand and combinations thereof.

The metal may especially be aluminum.

The metal oxide may especially be aluminum oxide ($Al_2O_3$), preferably of the corundum type.

The plastic may especially be a urea resin, phenolic resin, polyester resin or melamine resin.

The ceramic may especially be glass or a mixed ceramic.

The alloy may, for example, be steel, especially stainless steel. The alloy is preferably a nonrusting steel, especially nonrusting stainless steel. With regard to suitable stainless steels, reference is made to the description that follows.

The sand may especially be garnet sand.

The blasting agent preferably comprises a metal or an alloy, or the blasting agent preferably consists of a metal or an alloy. Such a blasting agent has the particular advantage that it does not break and therefore does not cause any notching of the surface of the medical product. On top of that, material transfer to the product surface can be reduced or even avoided entirely. Overall, this can additionally improve the corrosion resistance of the medical product and avoid the occurrence of unwanted intrinsic stresses in the product. Moreover, such a blasting agent is particularly suitable for increasing the scratch resistance of the medical product.

Preferably, the blasting agent comprises steel, especially stainless steel, or the blasting agent preferably consists of steel, especially stainless steel. Such a blasting agent can result in particularly stark manifestation of the advantages mentioned in the last paragraph.

In principle, the blasting agent may be of regular and/or irregular shape, especially in the form of blasting agent bodies of regular and/or irregular shape.

In addition, it is preferable that the blasting agent is free of corners and/or edges, especially in the form of corner- and/or edge-free blasting agent bodies. This can avoid the creation of notches on the surface of the medical product and therefore additionally improve the corrosion resistance thereof.

In principle, the blasting agent may be ellipsoidal, toroidal, spherical or bead-shaped, or be in the form of correspondingly configured blasting agent bodies.

The blasting agent is preferably spherical and/or bead-shaped or in the form of spherical and/or bead-shaped blasting agent bodies.

Alternatively or in combination, the blasting agent may have corners and/or edges. In particular, the blasting agent may be polyhedral, for example cubic, cuboidal, prism-shaped, pyramidal or parallelepiped-shaped, or take the form of correspondingly configured blasting agent bodies. The blasting agent may additionally take the form of a straight prism or oblique prism, or take the form of correspondingly configured blasting agent bodies.

Alternatively or in combination, the blasting agent may be conical and/or frustoconical, or take the form of conical and/or frustoconical blasting agent bodies.

Alternatively or in combination, the blasting agent may be in globular form, for example in the form of a rounded wire, or in the form of correspondingly configured blasting agent bodies.

Alternatively or in combination, the blasting agent may be in crushed form, especially in the form of crushed blasting agent bodies.

In addition, the blasting agent or blasting agent bodies may have at least one dimension, especially at least one average dimension, for example a diameter, especially average diameter, and/or a height, especially average height, and/or a length, especially average length, in the range from 40 μm to 2000 μm. The diameter of a spherical blasting agent or of spherical blasting agent bodies in the context of the present invention shall be understood here to mean twice the radius of a spherical blasting agent or of a single spherical blasting agent body. By contrast, the diameter of a nonspherical blasting agent or of nonspherical blasting agent bodies in the context of the present invention shall be understood to mean the greatest possible distance between two points that these can adopt relative to one another along a circumference line of a nonspherical blasting agent or of a single nonspherical blasting agent body. The average dimensions mentioned in this paragraph can be determined, for example, by means of laser diffraction or sieve analysis.

The blasting agent or blasting agent bodies can be accelerated onto the surface of the medical product, for example, by using jet blasting systems, injector blasting systems or wheel blasting systems. If a pressure jet or injector jet system is used, it is possible to use pressures of 1 bar to 6 bar.

In a further embodiment of the invention, the surface of the medical product is not electropolished.

Alternatively, the surface of the medical product may be electropolished, especially prior to the performance of step a), especially between a grinding operation, especially slide finishing and/or belt finishing, on the surface of the medical product and the performance of step a), especially between a treatment of the surface of the medical product with a blasting agent and the performance of step a), and/or after the performance of step a), especially between the performance of step a) and a treatment of the surface of the medical product with a passivating acid or a passivating acid-containing solution. The electropolishing is generally performed using an aqueous electrolyte solution. The aqueous electrolyte solution preferably comprises a mineral acid or a mineral acid mixture, especially selected from the group consisting of phosphoric acid, sulfuric acid and a mixture thereof. The aqueous electrolyte solution may also have a phosphoric acid content of 20% by weight to 70% by weight, especially 30% by weight to 60% by weight, preferably 40% by weight to 50% by weight, based on the total weight of the aqueous electrolyte solution, and/or a sulfuric acid content of 10% by weight to 70% by weight, especially 20% by weight to 60% by weight, preferably 30% by weight to 50% by weight, based on the total weight of the aqueous electrolyte solution. It is further preferable when the surface of the medical product is electropolished at a voltage, especially DC voltage, of 2 V to 10 V. The voltage here may be kept constant or varied during the electropolishing. It is further preferable when the surface of the medical product is electropolished at a current density of 5 A/dm$^2$ to 50 A/dm$^2$. It may further be preferable when the surface of the medical product is electropolished at a temperature of 50° C. to 65° C. With regard to the grinding mentioned in this paragraph, especially slide finishing and/or belt finishing, of the surface of the medical product and to the treatment of the surface of the medical product with a blasting agent, reference is made completely to the corresponding details given in the description so far. With regard to the treatment of the surface of the medical product with a passivating acid or a passivating acid-containing solution that has been mentioned in this paragraph, reference is made completely to the corresponding details given in the description which is still to follow.

Typically, step a) is performed by anodic removal of the surface of the medical product in an electrolyte solution, meaning that the medical product forms the anode in an electrochemical cell.

In a further embodiment of the invention, step a) is conducted more than once, especially twice, three times or four times.

This can particularly advantageously result in uniform processing of geometric peculiarities of the medical product, for example the closure of the medical product, without giving rise to relevant shadowing. The closure of the medical product can be processed in two positions in order to give rise to only minor shadows. Alternatively, it may be preferable that the medical product is articulated gradually during the performance of step a).

Alternatively, step a) can be conducted just once.

In a further embodiment of the invention, step a) is conducted using an acidic aqueous electrolyte solution, especially comprising a mineral acid or a mineral acid mixture.

In a further embodiment of the invention, the mineral acid is selected from the group consisting of phosphoric acid, sulfuric acid and a mixture thereof. A phosphoric acid-containing and/or sulfuric acid-containing aqueous electrolyte solution has been found here to be particularly advan-tageous for the electrochemical etching of the surface of a medical product made of stainless steel, especially corrosion-resistant stainless steel.

The acidic aqueous electrolyte solution may also be an aged acidic aqueous electrolyte solution.

Moreover, the acidic aqueous electrolyte solution may have a mineral acid content of 50% by weight to 95% by weight, especially 60% by weight to 95% by weight, preferably 75% by weight to 95% by weight, based on the total weight of the acidic aqueous electrolyte solution. In particular, the acidic aqueous electrolyte solution may have a phosphoric acid content of 10% by weight to 70% by weight, especially 20% by weight to 70% by weight, especially 30% by weight to 60% by weight, preferably 40% by weight to 50% by weight, and/or a sulfuric acid content of 10% by weight to 70% by weight, especially 20% by weight to 60% by weight, preferably 30% by weight to 50% by weight, based in each case on the total weight of the acidic aqueous electrolyte solution.

The acidic aqueous electrolyte solution may also include further additives, for example surface-active substances.

It is advantageous that the aggressiveness of the acidic aqueous electrolyte solution can be controlled via its water content. For example, the acidic aqueous electrolyte solution may have a water content of 5% by weight to 25% by weight, especially 5% by weight to 15% by weight, preferably 5% by weight to 10% by weight, based on the total weight of the acidic aqueous electrolyte solution.

In a further embodiment of the invention, step a) is conducted over a period of 6 min to 14 min, especially 8 min to 12 min, preferably 10 min.

In a further embodiment of the invention, step a) is conducted at/with a voltage, especially DC voltage, preferably measured at the anode (at the medical product to be surface-treated or -processed and/or manufactured), of <2 V, especially 1.2 V to 1.8 V, preferably 1.4 V to 1.7 V, more preferably 1.4 V to 1.5 V or 1.45 V to 1.65 V. In this embodiment of the invention, the advantages of the invention are particularly starkly manifested. The voltage is measured at the anode (at the medical product to be surface-treated or -processed and/or manufactured) preferably by means of a silver-silver chloride electrode. The voltages ascertained are then converted to a standard hydrogen electrode. Typically, the voltage is established at the current source without knowing which portion of the voltage is being applied to the anode and how much is being applied to residual resistances (for example wires, electrolyte, etc.). In the present invention, it is preferably the exact voltage at the anode which is crucial.

In addition, step a) may be conducted at/with a constant or varying voltage, especially DC voltage. With regard to suitable voltage ranges/values, reference is made to the voltages disclosed in the preceding paragraph.

In a further embodiment of the invention, step a) is conducted at/with a current density of 1.4 A/dm$^2$ to 2.4 A/dm$^2$, especially 1.6 A/dm$^2$ to 2.2 A/dm$^2$, preferably 1.8 A/dm$^2$ to 2.0 A/dm$^2$. By virtue of the (low) current densities disclosed in this paragraph, it is possible to particularly efficiently control etching of the surface of the medical product over time.

In a further embodiment of the invention, step a) is conducted at a temperature of 20° C. to 90° C., especially 50° C. to 80° C., preferably 70° C. to 80° C.

In a further embodiment of the invention, the surface of the medical product is not treated with a passivating acid or a passivating acid-containing solution, especially after performance of step a). This is because, as already mentioned, the etching step envisaged in accordance with the invention (step a)) can already particularly advantageously promote the formation of a passive layer on the surface of the medical product and therefore bring about an improvement in the corrosion resistance of the medical product. This configuration of the invention (likewise) has the advantage of a distinct reduction in processing/manufacturing times and/or costs for the medical product.

Alternatively, the surface of the medical product can be treated with a passivating acid or a passivating acid-containing solution, especially passivating acid-containing aqueous solution, especially after performance of step a), especially after electropolishing of the surface of the medical product. With regard to the electropolishing of the surface of the medical product that has been mentioned in this paragraph, reference is made completely to the corresponding details given in the description so far.

In this way, it is possible to additionally enhance or promote the formation of a passive layer on the surface of the medical product and therefore to additionally improve the corrosion resistance of the medical product. In the case of a medical product made from a chromium-containing or chromium-alloyed stainless steel, it is possible by means of a passivation layer, for example, to form thickened chromium oxide layers on the surface of the medical product.

Passivating acids used may, for example, be citric acid and/or nitric acid. The passivating acid-containing solution used may, for example, be an aqueous citric acid-containing solution, especially with a citric acid content of 5% by weight to 60% by weight, based on the total weight of the aqueous citric acid-containing solution. Alternatively, the passivating acid-containing solution used may be an aqueous nitric acid-containing solution, especially with a nitric acid content of 5% by weight to 60% by weight, based on the total weight of the aqueous nitric acid-containing solution.

The use of citric acid has advantages over the use of nitric acid both from a health point of view and from an occupational safety point of view. On top of that, by means of citric acid, in the case of medical products made of chromium-containing or chromium-alloyed stainless steel, it is possible to achieve thicker chromium oxide layers than is the case when nitric acid is used, since the latter also reduces the proportion of other alloy constituents in the case of such a stainless steel.

For performance of the passivation, the medical product can be immersed, for example, into the passivating acid or the passivating acid-containing solution. Alternatively, the passivating acid or the passivating acid-containing solution can be sprayed or poured onto the surface of the medical product.

In addition, the surface of the medical product can be treated with the passivating acid or passivating acid-containing solution over a period of 2 min to 120 min, especially 5 min to 60 min, preferably 10 min to 30 min.

In addition, the surface of the medical product can be treated with the passivating acid or passivating acid-containing solution within a temperature range from 20° C. to 80° C., especially 30° C. to 65° C., preferably 50° C. to 60° C.

In addition, a cleaning and/or degreasing operation on the surface of the medical product can be performed between step a) and the treatment of the surface of the medical product with the passivating acid or passivating acid-containing solution, especially between an electropolishing operation on the surface of the medical product and the treatment of the surface of the medical product with the passivating acid or passivating acid-containing solution. With regard to the electropolishing of the surface of the medical product that has been mentioned in this paragraph, reference is made completely to the corresponding details given in the description so far.

In a further embodiment of the invention, the performance of step a) is followed, especially after electropolishing of the surface of the medical product, especially after treatment of the surface of the medical product with a passivating acid or a passivating acid-containing solution, by a step b) of packing and/or marking, especially labeling, of the medical product. Preferably, a step ab) of sterilizing, especially steam sterilizing, of the medical product is performed between step a) and step b), especially between electropolishing of the surface of the medical product and step b), especially between a treatment of the surface of the medical product with a passivating acid or a passivating acid-containing solution. Alternatively, it may be preferable that performance of step b) is followed by performance of a step c) of sterilizing, especially steam sterilizing, of the medical product. With regard to the electropolishing of the surface of the medical product that has been mentioned in this paragraph and to the treatment of the surface of the medical product with a passivating acid or a passivating acid-containing solution that has been mentioned in this paragraph, reference is made completely to the corresponding details given in the description so far.

In a further embodiment of the invention, the medical product comprises steel, preferably stainless steel, or the medical product consists of steel, preferably stainless steel.

The expression "stainless steel" in the context of the present invention (in accordance with EN 10020) is understood to mean an alloyed or unalloyed steel having a particular level of purity, for example with a proportion by mass of sulfur and/or phosphorus of ≤0.025%, especially <0.025%.

The stainless steel may especially comprise at least one alloy element selected from the group consisting of chromium, nickel, molybdenum, titanium, niobium, tungsten, vanadium, cobalt and combinations thereof.

In particular, the stainless steel may have a proportion by mass of chromium of 10% to 25%.

Further preferably, the stainless steel is a nonrusting or corrosion-resistant stainless steel.

Further preferably, the stainless steel is a chromium-containing or chromium-alloyed stainless steel. Preferably, the stainless steel is a chromium-containing, corrosion-resistant stainless steel or a chromium-alloyed corrosion-resistant stainless steel.

In addition, the stainless steel may especially be a martensitic, ferritic or austenitic stainless steel.

Preferably, the stainless steel is a martensitic, corrosion-resistant stainless steel, especially what is called a carbon martensite, i.e. a corrosion-resistant stainless steel with chromium and carbon as the main alloy constituents, or what is called a nickel martensite, i.e. a corrosion-resistant stainless steel with nickel as the main alloy constituent, according to ISO 7153-1.

In particular, the stainless steel may be a martensitic stainless steel having a proportion by mass of chromium of 10.5% to 13% and/or a proportion by mass of carbon of 0.2% to 1%.

Alternatively, the stainless steel may especially be an austenitic stainless steel having a proportion by mass of chromium of 16% to 21% and/or a proportion by mass of carbon of 0.02% to 0.12%.

Alternatively, the stainless steel may especially be a ferritic stainless steel having a proportion by mass of chromium of 12% to 18% and/or a proportion by mass of carbon of <0.2%.

For example, the stainless steel may be a stainless steel having the short material designation X12Cr13 (materials number 1.4006). This is a martensitic stainless steel having a proportion by mass of carbon of 0.08% to 0.15%, a proportion by mass of chromium of 11.5% to 13.5%, and a proportion by mass of nickel of ≤0.75%.

Alternatively, the stainless steel may be a martensitic, corrosion-resistant stainless steel having the short material designation X12CrS13 (materials number 1.4005). This stainless steel has a proportion by mass of carbon of 0.08% to 0.15%, a proportion by mass of chromium of 12.0% to 14.0% and a proportion by mass of molybdenum of ≤0.60%, and optionally a proportion by mass of sulfur of 0.15% to 0.35%.

Alternatively, the stainless steel may be a martensitic, corrosion-resistant stainless steel having the short material designation X20Cr13 (materials number: 1.4021). This stainless steel has a proportion by mass of carbon of 0.16% to 0.25% and a proportion by mass of chromium of 12.0% to 14.0%.

Alternatively, the stainless steel may be a martensitic, corrosion-resistant stainless steel having the short material designation X15Cr13 (materials number: 1.4024). This stainless steel has a proportion by mass of carbon of 0.12% to 0.17% and a proportion by mass of chromium of 12.0% to 14.0%.

Alternatively, the stainless steel may be a martensitic, corrosion-resistant stainless steel having the short material designation X30Cr13 (materials number: 1.4028). This stainless steel has a proportion by mass of carbon of 0.26% to 0.35% and a proportion by mass of chromium of 12.0% to 14.0%.

Alternatively, the stainless steel may be a martensitic, corrosion-resistant stainless steel having the short material designation X46Cr13 (materials number: 1.4034). This stainless steel has a proportion by mass of carbon of 0.43% to 0.50% and a proportion by mass of chromium of 12.5% to 14.5%.

Alternatively, the stainless steel may be a martensitic, corrosion-resistant stainless steel having the short material designation X50CrMoV15 (materials number: 1.4116). This stainless steel has a proportion by mass of carbon of 0.45% to 0.55%, a proportion by mass of chromium of 14.0% to 15.0%, a proportion by mass of molybdenum of 0.50% to 0.80%, and a proportion by mass of vanadium of 0.10% to 0.20%.

Alternatively, the stainless steel may be a martensitic, corrosion-resistant stainless steel having the short material designation X17CrNi16-2 (materials number: 1.4057). This stainless steel has a proportion by mass of carbon of 0.12% to 0.22%, a proportion by mass of chromium of 15.0% to 17.0%, and a proportion by mass of nickel of 1.5% to 2.5%.

Alternatively, the stainless steel may be a martensitic, corrosion-resistant stainless steel having the short material designation X39CrMo17-1 (materials number: 1.4122). This stainless steel has a proportion by mass of carbon of 0.33% to 0.45%, a proportion by mass of chromium of 15.5% to 17.5%, a proportion by mass of molybdenum of 0.8% to 1.3%, and a proportion by mass of nickel of ≤1.0%.

Alternatively, the stainless steel may be a martensitic, corrosion-resistant stainless steel having the short material designation X14CrMoS17 (materials number: 1.4104). This stainless steel has a proportion by mass of carbon of 0.10% to 0.17%, a proportion by mass of chromium of 15.5% to 17.5%, a proportion by mass of molybdenum of 0.20% to 0.60%, and a proportion by mass of sulfur of 0.15% to 0.35%.

Alternatively, the stainless steel may be a martensitic, corrosion-resistant stainless steel having the short material designation X3CrNiMo13-4 (materials number: 1.4313). This stainless steel has a proportion by mass of carbon of ≤0.05%, a proportion by mass of chromium of 12.0% to 14.0%, a proportion by mass of molybdenum of 0.3% to 0.7%, and a proportion by mass of nickel of 3.5% to 4.5%.

Alternatively, the stainless steel may be a martensitic, corrosion-resistant stainless steel having the short material designation X4CrNiMo16-5-1 (materials number: 1.4418). This stainless steel has a proportion by mass of carbon of ≤0.06%, a proportion by mass of chromium of 15.0% to 17.0%, a proportion by mass of molybdenum of 0.80% to 1.50%, and a proportion by mass of nickel of 4.0% to 6.0%.

Alternatively, the stainless steel may be a martensitic stainless steel having the short material designation X65Cr13. This stainless steel has a proportion by mass of carbon of 0.58% to 0.70%, a proportion by mass of chromium of 12.5% to 14.5%, a proportion by mass of manganese of ≤1.00%, a proportion by mass of silicon of ≤1.00%, a proportion by mass of phosphorus of 0.04%, and a proportion by mass of sulfur of 0.015%.

Alternatively, the stainless steel may be a martensitic stainless steel having the short material designation X30CrMoN15-1 (materials number: 1.4108). This stainless steel has a proportion by mass of carbon of 0.25% to 0.35%, a proportion by mass of chromium of 14.0% to 16.0%, a proportion by mass of molybdenum of 0.85% to 1.10%, a proportion by mass of nickel of 0.50%, a proportion by mass of manganese of 1.00%, a proportion by mass of silicon of 1.00%, and a proportion by mass of nitrogen of 0.03% to 0.50%.

Alternatively, the stainless steel may be a martensitic stainless steel having the short material designation X70CrMo15 (materials number: 1.4109). This stainless steel has a proportion by mass of carbon of 0.60% to 0.75%, a proportion by mass of chromium of 14.0% to 16.0%, a proportion by mass of molybdenum of 0.40% to 0.80%, a proportion by mass of manganese of ≤1.00%, a proportion by mass of silicon of ≤0.70%, a proportion by mass of phosphorus of 0.04%, and a proportion by mass of sulfur of 0.015%.

Alternatively, the stainless steel may be a martensitic stainless steel having the short material designation X90CrMoV18 (materials number: 1.4112). This stainless steel has a proportion by mass of carbon of 0.90%, a proportion by mass of chromium of 17% to 19%, and a proportion by mass of molybdenum of 0.90%.

Alternatively, the stainless steel may be a martensitic stainless steel having the short material designation X38CrMoV15 (materials number: 1.4117). This stainless steel has a proportion by mass of carbon of 0.38%, a proportion by mass of chromium of 14% to 15%, and a proportion by mass of molybdenum of 0.50%.

Alternatively, the stainless steel may be a martensitic stainless steel having the short material designation X150CrMo17 (materials number: 1.4125). This stainless steel has a proportion by mass of carbon of 1.10%, a proportion by mass of chromium of 17%, and a proportion by mass of molybdenum of 0.60%.

Alternatively, the stainless steel may be a martensitic stainless steel having the short material designation X22CrMoNiS13-1 (materials number: 1.4121). This stainless steel has a proportion by mass of carbon of 0.20% to 0.25%, a proportion by mass of chromium of 12.0% to 14.0%, a proportion by mass of molybdenum of 1.00% to 1.50%, a proportion by mass of nickel of 0.80% to 1.20%, a proportion by mass of manganese of 1.00% to 1.50%, a proportion by mass of silicon of ≤1.00%, a proportion by mass of phosphorus of 0.045%, and a proportion by mass of sulfur of 0.15% to 0.25%.

Alternatively, the stainless steel may be a martensitic stainless steel having the short material designation X40CrMoVN16-2 (materials number: 1.4123). This stainless steel has a proportion by mass of carbon of 0.35% to 0.50%, a proportion by mass of chromium of 14.0% to 16.0%, a proportion by mass of molybdenum of 1.00% to 2.50%, a proportion by mass of nickel of 0.5%, a proportion by mass of manganese of ≤1.00%, a proportion by mass of silicon of ≤1.00%, a proportion by mass of phosphorus of 0.04%, and a proportion by mass of sulfur of 0.015%.

Alternatively, the stainless steel may be a martensitic stainless steel having the short material designation X105CrMo17 (materials number: 1.4125). This stainless steel has a proportion by mass of carbon of 0.95% to 1.20%, a proportion by mass of chromium of 16.0% to 18.0%, a proportion by mass of molybdenum of 0.04% to 0.80%, a proportion by mass of manganese of not more than 1.00%, a proportion by mass of silicon of not more than 1.00%, a proportion by mass of phosphorus of not more than 0.040%, and a proportion by mass of sulfur of not more than 0.015%.

Alternatively, the stainless steel may be a precipitation-hardening, corrosion-resistant stainless steel having the short material designation X5CrNiCuNb16-4 (materials number: 1.4542). This stainless steel has a proportion by mass of carbon of ≤0.07%, a proportion by mass of chromium of 15.0% to 17.0%, a proportion by mass of molybdenum of ≤0.60%, a proportion by mass of nickel of 3.0% to 5.0%, a proportion by mass of copper of 3.0% to 5.0%, and a proportion by mass of niobium of not more than 0.45%.

Alternatively, the stainless steel may be a precipitation-hardening, corrosion-resistant stainless steel having the short material designation X7CrNiAl17-7 (materials number: 1.4568). This stainless steel has a proportion by mass of carbon of ≤0.09%, a proportion by mass of chromium of 16.0% to 18.0%, a proportion by mass of nickel of 6.5% to 7.8%, and a proportion by mass of aluminum of 0.70% to 1.50%.

Alternatively, the stainless steel may be a precipitation-hardening, corrosion-resistant stainless steel having the short material designation X5CrNiMoCuNb14-5 (materials number: 1.4594). This stainless steel has a proportion by mass of carbon of ≤0.07%, a proportion by mass of chromium of 13.0% to 15.0%, a proportion by mass of molybdenum of 1.20% to 2.00%, a proportion by mass of nickel of 5.0% to 6.0%, a proportion by mass of copper of 1.20% to 2.00%, and a proportion by mass of niobium of 0.15% to 0.60%.

Alternatively, the stainless steel may be a precipitation-hardening, corrosion-resistant stainless steel having the short material designation X3CrNiTiMb12-9 (materials number: 1.4543). This stainless steel has a proportion by mass of carbon of ≤0.03%, a proportion by mass of chromium of 11.0% to 12.5%, a proportion by mass of molybdenum of ≤0.50%, a proportion by mass of nickel of 3.00% to 5.00%, a proportion by mass of titanium of ≤0.90% to 1.40%, a proportion by mass of copper of 1.50% to 2.50%, a proportion by mass of niobium of 0.10% to 0.50%, a proportion by mass of manganese of 0.50%, a proportion by mass of silicon of 0.50%, a proportion by mass of phosphorus of ≤0.02%, and a proportion by mass of sulfur of ≤0.015%.

Alternatively, the stainless steel may be a ferritic, corrosion-resistant stainless steel having the short material designation X2CrNi12 (materials number: 1.4003). This stainless steel has a proportion by mass of carbon of ≤0.03%, a proportion by mass of chromium of 10.5% to 12.5%, a proportion by mass of nickel of 0.3% to 1.00%, and a proportion of nitrogen of ≤0.03%.

Alternatively, the stainless steel may be a ferritic, corrosion-resistant stainless steel having the short material designation X2CrNi12 (materials number: 1.4512). This stainless steel has a proportion by mass of carbon of ≤0.03%, a proportion by mass of chromium of 10.5% to 12.5%, and a proportion by mass of titanium of not more than 0.65%.

Alternatively, the stainless steel may be a ferritic, corrosion-resistant stainless steel having the short material designation X6Cr17 (materials number: 1.4016). This stainless steel has a proportion by mass of carbon of ≤0.08% and a proportion by mass of chromium of 16.0% to 18.0%.

Alternatively, the stainless steel may be a ferritic, corrosion-resistant stainless steel having the short material designation X3CrTi17 (materials number: 1.4510). This stainless steel has a proportion by mass of carbon of ≤0.05%, a proportion by mass of chromium of 16.0% to 18.0%, and a proportion by mass of titanium of not more than 0.80%.

Alternatively, the stainless steel may be a ferritic, corrosion-resistant stainless steel having the short material designation X6CrMoS17 (materials number: 1.4105). This stainless steel has a proportion by mass of carbon of ≤0.08%, a proportion by mass of chromium of 16.0% to 18.0%, a proportion by mass of molybdenum of 0.20% to 0.60%, and a proportion by mass of sulfur of 0.15% to 0.35%.

Alternatively, the stainless steel may be a ferritic, corrosion-resistant stainless steel having the short material designation X3CrNb17 (materials number: 1.4511). This stainless steel has a proportion by mass of carbon of ≤0.05%, a proportion by mass of chromium of 16.0% to 18.0%, and a proportion by mass of niobium of not more than 1.00%.

Alternatively, the stainless steel may be a ferritic, corrosion-resistant stainless steel having the short material designation X2CrTiNb18 (materials number: 1.4509). This stainless steel has a proportion by mass of carbon of ≤0.03%, a proportion by mass of chromium of 17.5% to 18.5%, a proportion by mass of niobium of not more than 1.00%, and a proportion by mass of titanium of 0.10% to 0.60%.

Alternatively, the stainless steel may be a ferritic, corrosion-resistant stainless steel having the short material designation X6CrMo17-1 (materials number: 1.4113). This steel has a proportion by mass of carbon of ≤0.08%, a proportion by mass of chromium of 16.0% to 18.0%, and a proportion by mass of molybdenum of 0.90% to 1.40%.

Alternatively, the stainless steel may be a ferritic, corrosion-resistant stainless steel having the short material designation X2CrMoTi18-2 (materials number: 1.4521). This stainless steel has a proportion by mass of carbon of ≤0.025%, a proportion by mass of chromium of 17.0% to 20.0%, a proportion by mass of molybdenum of 1.80% to 2.50%, and a proportion by mass of titanium of not more than 0.80%.

Alternatively, the stainless steel may be an austenitic-ferritic, corrosion-resistant stainless steel having the short material designation X2CrNi22-2 (materials number: 1.4062). This stainless steel has a proportion by mass of carbon of ≤0.03%, a proportion by mass of chromium of 21.5% to 24.0%, a proportion by mass of molybdenum of ≤0.45%, a proportion by mass of nickel of 1.00% to 2.90%, and a proportion by mass of nitrogen of 0.16% to 0.28%.

Alternatively, the stainless steel may be an austenitic-ferritic, corrosion-resistant stainless steel having the short material designation X2CrMnNiN21-5-1 (materials number: 1.4162). This stainless steel has a proportion by mass of carbon of ≤0.04%, a proportion by mass of chromium of 21.0% to 22.0%, a proportion by mass of molybdenum of 0.10% to 0.80%, a proportion by mass of nickel of 1.35% to 1.70%, a proportion by mass of manganese of 4.0% to 6.0%, a proportion by mass of nitrogen of 0.20% to 0.25%, and a proportion by mass of copper of 0.10% to 0.80%.

Alternatively, the stainless steel may be an austenitic-ferritic, corrosion-resistant stainless steel having the short material designation X2CrNiN23-4 (materials number: 1.4362). This stainless steel has a proportion by mass of carbon of ≤0.03%, a proportion by mass of chromium of 22.0% to 24.0%, a proportion by mass of molybdenum of 0.10% to 0.60%, a proportion by mass of nickel of 3.5% to 5.5%, and a proportion by mass of copper of 0.10% to 0.60%.

Alternatively, the stainless steel may be an austenitic-ferritic, corrosion-resistant stainless steel having the short material designation X2CrNiMoN22-5-3 (materials number: 1.4462). This stainless steel has a proportion by mass of carbon of ≤0.03%, a proportion by mass of chromium of 21.0% to 23.0%, a proportion by mass of molybdenum of 2.5% to 3.5%, a proportion by mass of nickel of 4.5% to 6.5%, and a proportion by mass of nitrogen of 0.10% to 0.22%.

Alternatively, the stainless steel may be an austenitic-ferritic, corrosion-resistant stainless steel having the short material designation X2CrNiMnMoCuN24-4-3-2 (materials number: 1.4662). This stainless steel has a proportion by mass of carbon of ≤0.03%, a proportion by mass of chromium of 23.0% to 25.0%, a proportion by mass of molybdenum of 1.00% to 2.00%, a proportion by mass of nickel of 3.0% to 4.5%, a proportion by mass of manganese of 2.5% to 4.0%, and a proportion by mass of copper of 0.10% to 0.80%.

Alternatively, the stainless steel may be an austenitic-ferritic, corrosion-resistant stainless steel having the short material designation X2CrNiMoN25-7-4 (materials number: 1.4410). This stainless steel has a proportion by mass of carbon of ≤0.03%, a proportion by mass of chromium of 24.0% to 26.0%, a proportion by mass of molybdenum of 3.0% to 4.5%, a proportion by mass of nickel of 6.0% to 8.0%, and a proportion by mass of nitrogen of 0.24% to 0.35%.

Alternatively, the stainless steel may be an austenitic-ferritic, corrosion-resistant stainless steel having the short material designation X2CrNiMoCuWN25-7-4 (materials number: 1.4501). This stainless steel has a proportion by mass of carbon of ≤0.03%, a proportion by mass of chromium of 24.0% to 26.0%, a proportion by mass of molybdenum of 3.0% to 4.0%, a proportion by mass of nickel of 6.0% to 8.0%, a proportion by mass of copper of 0.50% to 1.00%, a proportion by mass of tungsten of 0.50% to 1.00%, and a proportion by mass of nitrogen of 0.20% to 0.30%.

Alternatively, the stainless steel may be an austenitic, corrosion-resistant stainless steel having the short material designation X2CrNiMo18-15-3 (materials number: 1.4441). This stainless steel has a proportion by mass of carbon of not more than 0.030%, a proportion by mass of chromium of 17.0% to 19.0%, a proportion by mass of molybdenum of 2.70% to 3.0%, a proportion by mass of nickel of 13.0% to 15.0%, a proportion by mass of manganese of not more than 2.00%, a proportion by mass of copper of not more than 0.50%, a proportion by mass of silicon of not more than 0.75%, a proportion by mass of phosphorus of not more than 0.025%, a proportion by mass of sulfur of not more than 0.003%, and a proportion by mass of nitrogen of not more than 0.10%.

Alternatively, the stainless steel may be an austenitic, corrosion-resistant stainless steel having the short material designation X5CrNi18-10 (materials number: 1.4301). This stainless steel has a proportion by mass of carbon of ≤0.07%, a proportion by mass of chromium of 17.5% to 19.5%, a proportion by mass of nickel of 8.0% to 10.5%, and a proportion by mass of nitrogen of ≤0.11%.

Alternatively, the stainless steel may be an austenitic, corrosion-resistant stainless steel having the short material designation X4CrNi18-12 (materials number: 1.4303). This stainless steel has a proportion by mass of carbon of ≤0.06%, a proportion by mass of chromium of 17.0% to 19.0%, a proportion by mass of nickel of 11.0% to 13.0%, and a proportion by mass of nitrogen of ≤0.11%.

Alternatively, the stainless steel may be an austenitic, corrosion-resistant stainless steel having the short material designation X8CrNiS18-9 (materials number: 1.4305). This stainless steel has a proportion by mass of carbon of ≤0.10%, a proportion by mass of chromium of 17.0% to 19.0%, a proportion by mass of nickel of 8.0% to 10.0%, a proportion by mass of sulfur of 0.15% to 0.35%, and a proportion by mass of copper of ≤1.00%.

Alternatively, the stainless steel may be an austenitic, corrosion-resistant stainless steel having the short material designation X2CrNi19-11 (materials number: 1.4306). This stainless steel has a proportion by mass of carbon of ≤0.030%, a proportion by mass of chromium of 18.0% to 20.0%, a proportion by mass of nickel of 10.0% to 12.0%, and a proportion by mass of nitrogen of ≤0.11%.

Alternatively, the stainless steel may be an austenitic, corrosion-resistant stainless steel having the short material designation X2CrNi18-9 (materials number: 1.4307). This stainless steel has a proportion by mass of carbon of ≤0.030%, a proportion by mass of chromium of 17.5% to 19.5%, a proportion by mass of nickel of 8.0% to 10.5%, and a proportion by mass of nitrogen of ≤0.11%.

Alternatively, the stainless steel may be an austenitic, corrosion-resistant stainless steel having the short material designation X2CrNi18-10 (materials number: 1.4311). This stainless steel has a proportion by mass of carbon of ≤0.030%, a proportion by mass of chromium of 17.5% to 19.5%, a proportion by mass of nickel of 8.5% to 11.5%, and a proportion by mass of nitrogen of 0.12% to 0.22%.

Alternatively, the stainless steel may be an austenitic, corrosion-resistant stainless steel having the short material designation X6CrNiTi18-10 (materials number: 1.4541). This stainless steel has a proportion by mass of carbon of ≤0.08%, a proportion by mass of chromium of 17.0% to 19.0%, a proportion by mass of nickel of 9.0% to 12.0%, and a proportion by mass of titanium of not more than 0.70%.

Alternatively, the stainless steel may be an austenitic, corrosion-resistant stainless steel having the short material designation X6CrNiNb18-10 (materials number: 1.4550). This stainless steel has a proportion by mass of carbon of ≤0.08%, a proportion by mass of chromium of 17.0% to 19.0%, a proportion by mass of nickel of 9.0% to 12.0%, and a proportion by mass of niobium of not more than 1.00%.

Alternatively, the stainless steel may be an austenitic, corrosion-resistant stainless steel having the short material designation X3CrNiCu18-9-4 (materials number: 1.4567). This stainless steel has a proportion by mass of carbon of ≤0.04%, a proportion by mass of chromium of 17.0% to 19.0%, a proportion by mass of nickel of 8.5% to 10.5%, and a proportion by mass of copper of 3.0% to 4.0%.

Alternatively, the stainless steel may be an austenitic, corrosion-resistant stainless steel having the short material designation X10CrNi18-8 (materials number: 1.4310). This stainless steel has a proportion by mass of carbon of 0.05% to 0.15%, a proportion by mass of chromium of 16.0% to 19.0%, a proportion by mass of molybdenum of ≤0.80%, and a proportion by mass of nickel of 6.0% to 9.5%.

Alternatively, the stainless steel may be an austenitic, corrosion-resistant stainless steel having the short material designation X5CrNiMo17-12-2 (materials number: 1.4401). This stainless steel has a proportion by mass of carbon of ≤0.07%, a proportion by mass of chromium of 16.5% to 18.5%, a proportion by mass of molybdenum of 2.00% to 2.50%, a proportion by mass of nickel of 10.0% to 13.0%, and a proportion by mass of nitrogen of ≤0.10%.

Alternatively, the stainless steel may be an austenitic, corrosion-resistant stainless steel having the short material designation X2CrNiMo17-12-2 (materials number: 1.4404). This stainless steel has a proportion by mass of carbon of ≤0.030%, a proportion by mass of chromium of 16.5% to 18.5%, a proportion by mass of molybdenum of 2.00% to 2.50%, a proportion by mass of nickel of 10.0% to 13.0%, and a proportion by mass of nitrogen of ≤0.10%.

Alternatively, the stainless steel may be an austenitic, corrosion-resistant stainless steel having the short material designation X6CrNiMoTi17-12-2 (materials number: 1.4571). This stainless steel has a proportion by mass of carbon of ≤0.08%, a proportion by mass of chromium of 16.5% to 18.5%, a proportion by mass of molybdenum of 2.00% to 2.50%, a proportion by mass of nickel of 10.5% to 13.5%, and a proportion by mass of titanium of not more than 0.70%.

Alternatively, the stainless steel may be an austenitic, corrosion-resistant stainless steel having the short material designation X2CrNiMoN17-13-3 (materials number: 1.4429). This stainless steel has a proportion by mass of carbon of ≤0.030%, a proportion by mass of chromium of 16.5% to 18.5%, a proportion by mass of molybdenum of 2.5% to 3.0%, a proportion by mass of nickel of 11.0% to 14.0%, and a proportion by mass of nitrogen of 0.12% to 0.22%.

Alternatively, the stainless steel may be an austenitic, corrosion-resistant stainless steel having the short material designation X2CrNiMo18-14-3 (materials number: 1.4435). This stainless steel has a proportion by mass of carbon of ≤0.030%, a proportion by mass of chromium of 17.0% to 19.0%, a proportion by mass of molybdenum of 2.5% to 3.0%, a proportion by mass of nickel of 12.5% to 15.0%, and a proportion by mass of nitrogen of ≤0.10%.

Alternatively, the stainless steel may be an austenitic, corrosion-resistant stainless steel having the short material designation X3CrNiMo17-13-3 (materials number: 1.4436). This stainless steel has a proportion by mass of carbon of ≤0.05%, a proportion by mass of chromium of 16.5% to 18.5%, a proportion by mass of molybdenum of 2.5% to 3.0%, a proportion by mass of nickel of 10.5% to 13.0%, and a proportion by mass of nitrogen of ≤0.10%.

Alternatively, the stainless steel may be an austenitic, corrosion-resistant stainless steel having the short material designation X2CrNiMoN17-13-5 (materials number: 1.4439). This stainless steel has a proportion by mass of carbon of ≤0.030%, a proportion by mass of chromium of 16.5% to 18.5%, a proportion by mass of molybdenum of 4.0% to 5.0%, a proportion by mass of nickel of 12.5% to 14.5%, and a proportion by mass of nitrogen of 0.12% to 0.22%.

Alternatively, the stainless steel may be an austenitic, corrosion-resistant stainless steel having the short material designation X1NiCrMoCu25-20-5 (materials number: 1.4539). This stainless steel has a proportion by mass of carbon of ≤0.020%, a proportion by mass of chromium of 19.0% to 21.0%, a proportion by mass of molybdenum of 4.0% to 5.0%, a proportion by mass of nickel of 24.0% to 26.0%, a proportion by mass of copper of 1.20% to 2.00%, and a proportion by mass of nitrogen of ≤0.15%.

Alternatively, the stainless steel may be an austenitic, corrosion-resistant stainless steel having the short material designation X2CrNiMnMoNbN25-18-5-4 (materials number: 1.4565). This stainless steel has a proportion by mass of carbon of ≤0.030%, a proportion by mass of chromium of 24.0% to 26.0%, a proportion by mass of molybdenum of 4.0% to 5.0%, a proportion by mass of nickel of 16.0% to 19.0%, a proportion by mass of manganese of 5.0% to 7.0%, a proportion by mass of nitrogen of 0.30% to 0.60%, and a proportion by mass of niobium of ≤0.15%.

Alternatively, the stainless steel may be an austenitic, corrosion-resistant stainless steel having the short material designation X1NiCrMoCuN25-20-7 (materials number: 1.4529). This stainless steel has a proportion by mass of carbon of ≤0.020%, a proportion by mass of chromium of 19.0% to 21.0%, a proportion by mass of molybdenum of 6.0% to 7.0%, a proportion by mass of nickel of 24.0% to 26.0%, a proportion by mass of copper of 0.50% to 1.50%, and a proportion by mass of nitrogen of 0.15% to 0.25%.

Alternatively, the stainless steel may be an austenitic, corrosion-resistant stainless steel having the short material designation X1CrNiMoCuN20-18-7 (materials number: 1.4547). This stainless steel has a proportion by mass of carbon of ≤0.020%, a proportion by mass of chromium of 19.5% to 20.5%, a proportion by mass of molybdenum of 6.0% to 7.0%, a proportion by mass of nickel of 17.5% to 18.5%, a proportion by mass of copper of 0.50% to 1.00%, and a proportion by mass of nitrogen of 0.18% to 0.25%.

Alternatively, the stainless steel may be an austenitic, corrosion-resistant stainless steel having the short material designation X1CrNiMoCuN24-22-8 (materials number: 1.4652). This stainless steel has a proportion by mass of carbon of ≤0.020%, a proportion by mass of chromium of 23.0% to 25.0%, a proportion by mass of molybdenum of 7.0% to 8.0%, a proportion by mass of nickel of 21.0% to 23.0%, a proportion by mass of manganese of 2.0% to 4.0%, and a proportion by mass of nitrogen of 0.45% to 0.55%.

In a further embodiment of the invention, the medical product is a medical, preferably surgical, instrument. The instrument may be a reusable instrument or a single-use instrument.

In addition, the instrument may be a minimally invasive instrument, i.e. an instrument usable in minimally invasive surgery.

The surgical instrument may especially be selected from the group consisting of a spreading instrument, gripping instrument, clamping instrument, cutting instrument, sewing device, endoscope and combined instrument.

The spreading instrument may, for example, be a surgical hook, a retractor, a wound spreader, a sternal spreader, a wound closer, a speculum or a trocar sleeve.

The gripping instrument may, for example, be a set of tweezers, a clamp, a needle holder or a set of grasping forceps.

The clamping instrument may, for example, be a soft clamp, especially for temporary occlusion of the intestine and fine vessels, or a preparatory clamp.

The cutting instrument may, for example, be a scalpel, a knife, a set of shears, a set of branch forceps, a set of bone splinter forceps, a set of ring forceps, an electrotome, a conchotome, a cauter or an ultrasonic knife.

The sewing device may especially be a stapler or a staple remover.

The combined instrument may be an endostapler or a stapler which, for example, clamps and simultaneously precisely cuts a hollow organ. In addition, the combined instrument may be a combined needle holder which, as a universal sewing device, can both grip and cut.

Moreover, the surgical instrument may be a hammer.

Moreover, the surgical instrument may be a chisel, especially a flat chisel or gouge, such as a bone gouge, or a curette, especially a bone curette.

Moreover, the surgical instrument may be a probe.

Moreover, the surgical instrument may be a bone punch.

Moreover, the surgical instrument may be a lever or elevator or a raspatory.

In a second aspect, the invention relates to a medical product comprising or consisting of a metal or an alloy, wherein the medical product is produced or producible by a method according to the first aspect of the invention and/or has at least one of the following features:

a pitting corrosion potential of 100 mV to 1200 mV, especially 200 mV to 800 mV, preferably 400 mV to 500 mV (measured against a standard hydrogen electrode)

and/or a contact angle of 90° to 140°, especially 100° to 130°, preferably 110° to 130°, and/or a passive layer, especially of chromium oxide, having a thickness of 1 nm to 10 nm, especially 3 nm to 10 nm, preferably 5 nm to 10 nm, which coats at least sections of the surface of the medical product, especially only in sections or completely.

The aforementioned pitting corrosion potentials and contact angles are particularly advantageous with regard to the corrosion resistance of the medical product.

The expression "pitting corrosion potential" in the context of the present invention is understood to mean the electrochemical potential, which can be determined with an electrochemical cell using a three-electrode arrangement. Pitting corrosion potential is characterized by a rapid rise in current and here describes the collapse of the passive layer with onset of pitting corrosion. An increase in pitting corrosion potential results in an improvement in corrosion resistance through a reduction in propensity to pitting corrosion.

Pitting corrosion potential can be measured according to ASTM G5-13-1 or DIN EN ISO 10993-15.

The expression "contact angle" in the context of the present invention shall be understood to mean the angle formed by a liquid droplet on the surface of the medical product with respect to the surface thereof. A reduced contact angle is associated with reduced contact of the liquid droplet on the surface of the medical product. A reduction in contact angle particularly advantageously results in an improvement in corrosion resistance and cleanability of the medical product.

The contact angle can be measured according to ASTM D 7334-08. Alternatively, the measurement of the contact angle can be conducted by means of a contact angle measuring instrument available from dataPhysics under the trademark CONTACT ANGLE SYSTEM OCA 15 PLUS™ and using a 0.9% sodium chloride solution (B. Braun), with a droplet volume of 1 μl. For measurement of the contact angle, the samples in this case may be washed in a regular manufacturing process and cleaned prior to the measurement in demineralized water in an ultrasound bath for 5 minutes, with rinsing of the samples with demineralized water and blowing dry with oil-free compressed air directly prior to the measurement.

The medical product is preferably a medical, preferably surgical, instrument.

With regard to further features and advantages of the medical product, for avoidance of repetition, reference is made completely to the details given in the context of the first aspect of the invention. The features and advantages described therein in relation to the method and the medical product are also applicable mutatis mutandis to the medical product according to the second aspect of the invention.

DETAILED DESCRIPTION

Further features and advantages of the invention will be apparent from the description of preferred embodiments with reference to examples that follows. It is possible here for features of the invention each to be implemented on their own or in combination with one another. The embodiments described hereinafter serve to further elucidate the invention without restriction thereto.

EXAMPLES

1. Surface Treatment of a Surgical Instrument or Representative Specimen by a Method of the Invention The specimens used, and also surgical instruments, were produced from identical martensitic nonrusting steel (X20Cr13) and by identical manufacturing steps and parameters.

SEM/EDX analyses (extraneous material and doubled-over material) were conducted on the instruments and sample platelets.

Potentiodynamic tests (pitting corrosion potential) were likewise conducted on the instruments and sample platelets.

Contact angle measurements (contact angle) were conducted on sample platelets (planar surface without shadows).

Gloss measurement (gloss) was conducted on sample platelets (planar surface without shadows).

3D laser confocal microscopy (roughness depth) was conducted on sample platelets (planar surface without shadows).

Prior to the surface treatment, surgical instruments, corrosion specimens and sample platelets according to the current production chain of surgical instruments were shaped and heat-treated.

For subsequent surface treatment, a surgical instrument (BH110R clamp), a corrosion specimen and sample platelets were treated by means of slide finishing in acidic solution over a period of four hours and then brightened by slide finishing in aqueous solution over a period of one hour.

Thereafter, the surgical instruments, corrosion specimens and sample platelets were electrochemically etched. For this purpose, the parts were immersed into an acidic aqueous electrolyte solution having a mineral acid content of 11% by weight of phosphoric acid and 61% by weight of sulfuric acid that was at a temperature of 40° C., and a DC voltage was applied for 10 minutes, so as to result in a voltage of 1.5 V at the anode. A current density of 2.0 A/dm$^2$ was established here.

Finally, the surgical instruments, corrosion specimens and sample platelets were passivated. For this purpose, the parts were immersed into a 10% by weight citric acid solution at a temperature of 60° C. for 10 minutes. Thereafter, the parts were pickled and cleaned in ethanol.

After the production, the formation of the surface of instruments and sample platelets was examined via scanning electron microscopy with an energy-dispersive x-ray spectroscopy unit. The SEM studies showed etching trenches distributed virtually randomly over the surface with slight localization at the grain boundaries. These were in the order of magnitude range of about 5 μm. The chemical composition was homogeneous and had a lower chromium level compared to the starting material at about 0.1% by weight. This was because of the chromium carbides leached out of the surface.

In addition, the topography of the surface on the instruments and sample platelets was assessed by means of 3D laser confocal microscopy and by metallographic sections. By means of the 3D laser confocal measurements, it was possible to determine an average roughness depth of 0.5 μm. This was attributable to the depth of the etching trenches which, according to the metallographic studies, were in the range of 1-3 μm.

The change in the reflection characteristics was examined by a gloss measurement on the test platelets. A distinct reduction in gloss was found with values of 3.7 gloss units (20°) and 21.6 gloss units (60°). The reflection characteristics could thus be determined as being strongly matt.

Analysis of the wetting by liquids was accomplished by contact angle measurement on the test platelets. An average contact angle of 116.3° was determined here.

Finally, the electrochemical/corrosive characteristics of the surface formed were examined by potentiodynamic polarization measurements on corrosion specimens, and pitting corrosion potential was ascertained. For comparison as to whether the measurements that were measured on test specimens relate to the instrument, pitting corrosion potential was measured on a laboratory instrument. The results for the test specimens were confirmed here. It was possible here to record a pitting corrosion potential of 475 mV.

2. Surface Treatment of a Surgical Instrument by a Method of the Generic Type A surgical instrument (BH110R clamp), corrosion specimens and sample platelets were first treated by means of slide finishing over a period of four hours. Thereafter, the surgical instrument and the specimens were brightened over a period of one hour.

Thereafter, the surgical instrument and the specimens were treated by means of blasting. For this purpose, glass beads having an average diameter of 40 μm to 70 μm were used. The blasting was conducted in an injector blasting system under a pressure of 4 bar.

Subsequently, the surgical instrument and the specimens were subjected to passivation. For this purpose, a 10% citric acid solution was used. The passivating was effected at a temperature of 55° C. over a period of 10 minutes.

On conclusion of the surface treatment of the surgical instrument and of the specimens, many instances of doubled-over material or overlapping material were detectable. In addition, an extraneous material transfer of 1.4% was detected. The roughness depth was in the region of 0.151 μm. In addition, the sample platelets had a contact angle of 66.0°. The gloss was found to be 41.9 gloss units (20°) and 159.8 gloss units (60°), and could thus be described as slightly matt. The pitting corrosion potential of the corrosion specimens was 386 mV.

3. Conclusion

The above-described comparison of a method of the invention and of a method of the generic type shows that the method of the invention leads to more corrosion-resistant products with very low reflectance (gloss).

The invention claimed is:

1. A method of surface treating and/or producing a precursor or a component of a surgical instrument, the precursor or the component of the surgical instrument comprising a metal or an alloy, the method comprising the steps of:

slide finishing a surface of the precursor or the component of the surgical instrument; and electrochemically etching the precursor or the component of the surgical instrument at a voltage applied to an anode of 1.4 V to 1.7 V and/or at a current density of 1.6 A/dm$^2$ to 2.2 A/dm$^2$, wherein the step of electrochemically etching the precursor or the component of the surgical instrument reduces reflection of light from the precursor or the component of the surgical instrument.

2. The method according to claim 1, wherein the step of electrochemically etching the precursor or the component of the surgical instrument is preceded by a grinding operation on the surface of the precursor or the component of the surgical instrument.

3. The method according to claim 1, wherein the surface of the precursor or the component of the surgical instrument is not treated with a blasting agent and/or is not electropolished to increase surface smoothness.

4. The method according to claim 1, wherein the step of electrochemically etching the precursor or the component of the surgical instrument is performed using an acidic aqueous electrolyte solution.

5. The method according to claim 1, wherein a surface of the precursor or the component of the surgical instrument is not treated with a passivating acid or a passivating acid-containing solution.

6. The method according to claim 1, wherein the step of electrochemically etching the precursor or the component of the surgical instrument is followed by the steps of:

packing the precursor or the component of the surgical instrument; and sterilizing the precursor or the component of the surgical instrument.

7. The method according to claim 6, wherein the step of sterilizing the precursor or the component of the surgical instrument is performed prior to the step of packing the precursor or the component of the surgical instrument.

8. The method according to claim 1, wherein the precursor or the component of the surgical instrument comprises a stainless steel.

9. The method according to claim 8, wherein the stainless steel is a martensitic, corrosion-resistant stainless steel.

10. The method according to claim 1, wherein the step of electrochemically etching the precursor or the component of the surgical instrument is preceded by the step of:

belt finishing on the surface of the precursor or the component of the surgical instrument.

11. A method of surface treating and/or producing a precursor or a component of a surgical instrument, the precursor or the component of the surgical instrument comprising a metal or an alloy, the method comprising the steps of:

slide finishing a surface of the precursor or the component of the surgical instrument; and electrochemically etching the precursor or the component of the surgical instrument at a voltage applied to an anode of 1.4 V to 1.7 V and/or at a current density of 1.6 A/dm$^2$ to 2.2 A/dm$^2$, wherein the step of electrochemically etching the precursor or the component of the surgical instrument forms a roughened product surface that scatters incident light.

12. A method of surface treating and/or producing a precursor or a component of a surgical instrument, the precursor or the component of the surgical instrument comprising a metal or an alloy, the method comprising the steps of:

slide finishing a surface of the precursor or the component of the surgical instrument; and electrochemically etching the precursor or the component of the surgical instrument at a voltage applied to an anode of 1.4 V to 1.7 V and/or at a current density of 1.6 A/dm$^2$ to 2.2 A/dm$^2$, wherein the step of electrochemically etching the precursor or the component of the surgical instrument forms a microstructure comprising open etching pits.

13. The method according to claim 1, wherein the step of slide finishing the surface of the precursor or the component of the surgical instrument comprises introducing the precursor or the component of the surgical instrument into a vessel together with slide finishing bodies.

14. The method according to claim 13, wherein the slide finishing bodies are contained in an aqueous solution.

15. The method according to claim 14, wherein the aqueous solution contains an additive selected from the group consisting of anticorrosives, degreasing agents, pickling agents, separating agents, and mixtures thereof.

16. The method according to claim 13, further the step of slide finishing the surface of the precursor or the component of the surgical instrument further comprises displacing the precursor or the component of the surgical instrument relative to the slide finishing bodies to cause abrasion of material.

17. The method according to claim 13, wherein the slide finishing bodies comprise material selected from the group consisting of ceramic, plastic, natural products, and steel.

18. The method according to claim 13, wherein the slide finishing bodies are free of corners and edges.

19. The method according to claim 13, wherein the slide finishing bodies comprise corners and edges.

20. The method according to claim 1, wherein the step of slide finishing the surface of the precursor or the component of the surgical instrument comprises barrel finishing, vibratory finishing, plunge finishing, drag finishing, centrifugal finishing or pressure flow lapping.

21. The method according to claim 1, wherein the step of slide finishing the surface of the precursor or the component of the surgical instrument comprises slide finishing in acidic solution.

22. The method according to claim 21, wherein the step of slide finishing the surface of the precursor or the component of the surgical instrument further comprises slide finishing in aqueous solution after slide finishing in acidic solution.

23. A method of surface treating and/or producing a precursor or a component of a surgical instrument, the precursor or the component of the surgical instrument comprising a metal or an alloy, the method comprising the step of:

electrochemically etching the precursor or the component of the surgical instrument at a voltage applied to an anode of 1.4 V to 1.7 V and/or at a current density of 1.6 A/dm$^2$ to 2.2 A/dm$^2$, wherein the step of electrochemically etching the precursor or the component of the surgical instrument reduces reflection of light from the precursor or the component of the surgical instrument, wherein the precursor or the component of the surgical instrument comprises a stainless steel, and wherein the stainless steel is a martensitic, corrosion-resistant stainless steel.

\* \* \* \* \*